United States Patent
Nicot et al.

(10) Patent No.: US 10,534,055 B2
(45) Date of Patent: Jan. 14, 2020

(54) NMR METHOD FOR DETERMINING NON-OIL VOLUME OF A ROCK SAMPLE

(71) Applicant: TOTAL SA, Courbevoie (FR)

(72) Inventors: Benjamin Nicot, Pau (FR); Jean-Pierre Korb, Yerres (FR); Bérangère Rousseau, Noisy-sur-ecole (FR)

(73) Assignee: TOTAL SA, Courbevoie (FR)

( * ) Notice: Subject to any disclaimer, the term of this patent is extended or adjusted under 35 U.S.C. 154(b) by 90 days.

(21) Appl. No.: 15/320,083

(22) PCT Filed: Jun. 9, 2015

(86) PCT No.: PCT/EP2015/062780
§ 371 (c)(1),
(2) Date: Dec. 19, 2016

(87) PCT Pub. No.: WO2015/193142
PCT Pub. Date: Dec. 23, 2015

(65) Prior Publication Data
US 2017/0139027 A1    May 18, 2017

(30) Foreign Application Priority Data
Jun. 19, 2014    (EP) .................... 14305947

(51) Int. Cl.
*G01R 33/50* (2006.01)
*G01N 33/24* (2006.01)
*G01N 24/08* (2006.01)

(52) U.S. Cl.
CPC .......... *G01R 33/50* (2013.01); *G01N 24/081* (2013.01); *G01N 33/246* (2013.01)

(58) Field of Classification Search
CPC ............ G01N 24/081; G01N 15/0886; G01N 2015/0813; G01N 2035/00881;
(Continued)

(56) References Cited

U.S. PATENT DOCUMENTS

| 8,395,384 B2* | 3/2013 | Fransson ............. G01N 24/081 324/303 |
| 2013/0113480 A1* | 5/2013 | Kadayam ................ G01V 3/32 324/303 |

(Continued)

FOREIGN PATENT DOCUMENTS

| EP | 0 544 585 A1 | 6/1993 |
| EP | 2 765 409 A1 | 8/2014 |
| WO | WO 2013/037093 A1 | 3/2013 |

OTHER PUBLICATIONS

International Search Report for PCT/EP2015/062780, dated Aug. 19, 2015, 4 pages.
Written Opinion for PCT/EP2015/062780, dated Aug. 19, 2015, 9 pages.
Washburn Kathryn E et al: "Updated methodology for nuclear magnetic resonance characterization of shales", Journal of Magnetic Resonance, vol. 233, May 4, 2013 (May 4, 2013), pp. 17-28, XP028674013, ISSN: 1090-7807, DOI: 10.1016/J.JMR.2013.04. 014.
(Continued)

*Primary Examiner* — G. M. A Hyder
(74) *Attorney, Agent, or Firm* — Patterson Thuente Pedersen, P.A.

(57) ABSTRACT

The present invention relates to a method for determining a non-oil volume of a rock sample comprising: receiving a rock sample; and receiving a non-oil zone in a NMR map using a T1T2 sequence, the non-oil zone being associated to non-oil in the map; Then, determining a first NMR map of the received rock sample using a T1T2 sequence, and determining a volume of non-oil in the received rock sample based on an integral in an integration zone of the firstNMR map. The integration zone of the first NMR map being determined based on the received non-oil zone, and a calibration value.

7 Claims, 7 Drawing Sheets

(58) Field of Classification Search
CPC .... G01N 24/082; G01N 33/24; G01N 33/246; G01V 3/32; G01V 3/14; G01R 33/50; G01R 33/448
See application file for complete search history.

(56) References Cited

U.S. PATENT DOCUMENTS

| | | | | |
|---|---|---|---|---|
| 2013/0271127 | A1* | 10/2013 | Dangfa | G01V 3/32 324/303 |
| 2014/0055134 | A1* | 2/2014 | Fordham | G01R 33/4818 324/309 |
| 2014/0340082 | A1* | 11/2014 | Yang | G01N 24/081 324/309 |
| 2015/0198036 | A1* | 7/2015 | Kleinberg | G01N 15/0886 702/12 |
| 2016/0290942 | A1* | 10/2016 | Wang | G01N 24/081 |
| 2016/0341680 | A1* | 11/2016 | Kadayam | G01N 24/081 |

OTHER PUBLICATIONS

Jonathan Mitchell et al: "Quantitative In Situ Enhanced Oil Recovery Monitoring Using Nuclear Magnetic Resonance", Transport in Porous Media, vol. 94, No. 3, May 23, 2012 (May 23, 2012), p. 683-706, XP035098658, Kluwer Academic Publishers, Do ISSN; 1573-1634, DOI: 10.1007/S11242-012-0019-8.

Mai A et al; "SPE 75687; On the Characterization of Carbonate Reservoirs Using Low Field NMR Tools", SPE Annual Technical Conference and Exhibition, Jan. 1, 2002 (Jan. 1, 2002), pp. 487-497, XP009034280.

Meridji Y et al: "SPE 168073: Fluid identification in complex clastic reservoirs using 2d NMR Maps: A case study from Saudi Arabia", Society of Petroleum Engineers, 2013, pp. 1-14, XP002743469, SPE Saudi Arabia Section Technical Symposium and Exhibition 2013 USA.

* cited by examiner

NMR METHOD FOR DETERMINING NON-OIL VOLUME OF A ROCK SAMPLE

RELATED APPLICATIONS

The present application is a National Phase entry of PCT Application No. PCT/EP2015/062780 filed Jun. 9, 2015, which claims priority from EP Patent Application No. 14305947.5, filed Jun. 19, 2014, said applications being hereby incorporated by reference herein in their entirety.

BACKGROUND OF THE INVENTION

The present invention relates to the domain of the estimation of hydrocarbon (i.e. oil) resources in the subsoil and especially the domain of the determination of oil saturation in the sub soil.

The approaches described in this section could be pursued, but are not necessarily approaches that have been previously conceived or pursued. Therefore, unless otherwise indicated herein, the approaches described in this section are not prior art to the claims in this application and are not admitted to be prior art by inclusion in this section. Furthermore, all embodiments are not necessarily intended to solve all or even any of the problems brought forward in this section.

Determining the volume of the fluids (water, oil, etc.) in the subsoil may be a key factor to adequately estimate the economic value of a given field: in particular, hydrocarbon production depends on porosity, saturation, wettability, pore pressure, matrix permeability and hydraulic fractures.

It may be important to distinguish the different fluids in the subsoil as each fluid has a different economic value and can have a different impact on the dynamics of the production.

Mineralogical variations, low permeability and the multiscale microstructure of the organic kerogen may also complicate the evaluation of these rocks.

Most of the known technics used to estimate the volume of fluids in the subsoil are based on simulations (and can be inaccurate) or are based on destructive analysis of rock samples (and thus, the rock samples cannot be used for other purposes).

If NMR technics may be known, it may be difficult to distinguish the oil and water in the NMR responses.

There is thus a need for non-invasively determining the surface dynamics of petroleum fluids (oil/water/gas) trapped in the complex microstructure of an oil-shale rock by analyzing the oil/water saturation of the subsoil.

SUMMARY OF THE INVENTION

The invention relates to a method for determining a non-oil volume of a rock sample comprising:
  receiving a rock sample;
  receiving a non-oil zone in a NMR map using a $T_1T_2$ sequence, said non-oil zone being associated to non-oil in said map;
  determining a first NMR map of said received rock sample using a $T_1T_2$ sequence;
  determining a volume of non-oil in the received rock sample based on an integral in an integration zone of the first NMR map and a calibration value.

Said integration zone of the first NMR map may be determined based on the received non-oil zone.

Nuclear magnetic resonance (NMR) is a physical phenomenon in which nuclei/proton in a magnetic field absorb and re-emit electromagnetic radiation during the relaxation phase.

The received rock sample is, most of the time, extracted from a drilling of a real subsoil.

The non-oil zone is a zone where the operator considers that the signal of the NRM map does not correspond to the hydrocarbon signal. In the below description, the "non-oil" is often consider to be water or a similar liquid.

The NMR map using a $T_1T_2$ sequence is also known as $T_1T_2$ map.

Thus, without any invasive analysis, it is possible to determine the non-oil (or water) volume of a given rock sample.

In addition, the volume of non-oil may be determined based on a ratio of the integral in the integration zone of the first NMR map by the calibration value.

In one possible embodiment, it is also possible to determine the water saturation of said rock sample based on the above method.

Therefore, the invention also relates to a method for determining an water saturation value of a rock sample comprising:
  determining a non-oil volume of said rock sample according to the above mentioned method;
  determining a porosity value of said rock sample;
  determining a water saturation value based on the determined volume of non-oil, the determined porosity value and a volume of the rock sample.

The porosity may be determined according to standard method such as pychnometry or with the following method.

Indeed, the determination of the porosity value may be performed by a method comprising:
  saturating said rock sample with a saturation fluid;
  determining a saturated NMR map of the saturated rock sample using a $T_1T_2$ sequence;
  determining the porosity value based on an integral in an integration zone of the saturated NMR map, the calibration value and a volume of the rock sample.

Said integration zone of the saturated NMR map may be determined based on the received non-oil zone.

In addition, the porosity value may be determined based on a ratio:
  of the integral in the integration zone of the saturated NMR map;
  by the product of the calibration value by the volume of the rock sample.

The water saturation value may be function of the ratio of the determined volume of non-oil over the volume of the rock sample divided by the porosity value.

Moreover, the saturation fluid may be brine.

Another aspect of the invention relates to a device for determining a non-oil volume ($v_{water}$) of a rock sample comprising:
  an interface for receiving a rock sample (101);
  an interface for receiving a non-oil zone (110) in a NMR map using a $T_1T_2$ sequence, said non-oil zone being associated to non-oil in said map;
  a NMR device for determining (102) a first NMR map of said received rock sample using a $T_1T_2$ sequence;
  a circuit for determining (108a) a volume of non-oil ($v_{water}$) in the received rock sample based on an integral in an integration zone of the first NMR map, said integration zone of the first NMR map being determined based on the received non-oil zone, and a calibration value (K).

The saturation process of the rock sample may not be directly performed by said device (this device may for instance be a computer machine).

A third aspect relates to a computer program product comprising a computer readable medium, having thereon a computer program comprising program instructions. The computer program is loadable into a data-processing unit and adapted to cause the data-processing unit to carry out the method described above when the computer program is run by the data-processing unit.

Other features and advantages of the method and apparatus disclosed herein will become apparent from the following description of non-limiting embodiments, with reference to the appended drawings.

BRIEF DESCRIPTION OF THE DRAWINGS

The present invention is illustrated by way of example, and not by way of limitation, in the figures of the accompanying drawings, in which like reference numerals refer to similar elements and in which.

DESCRIPTION OF PREFERRED EMBODIMENTS

It is proposed to use the nuclear magnetic relaxation $T_1T_2$ maps to measure the quantity of liquids (water/oil) contained in a rock sample.

Figure 1:
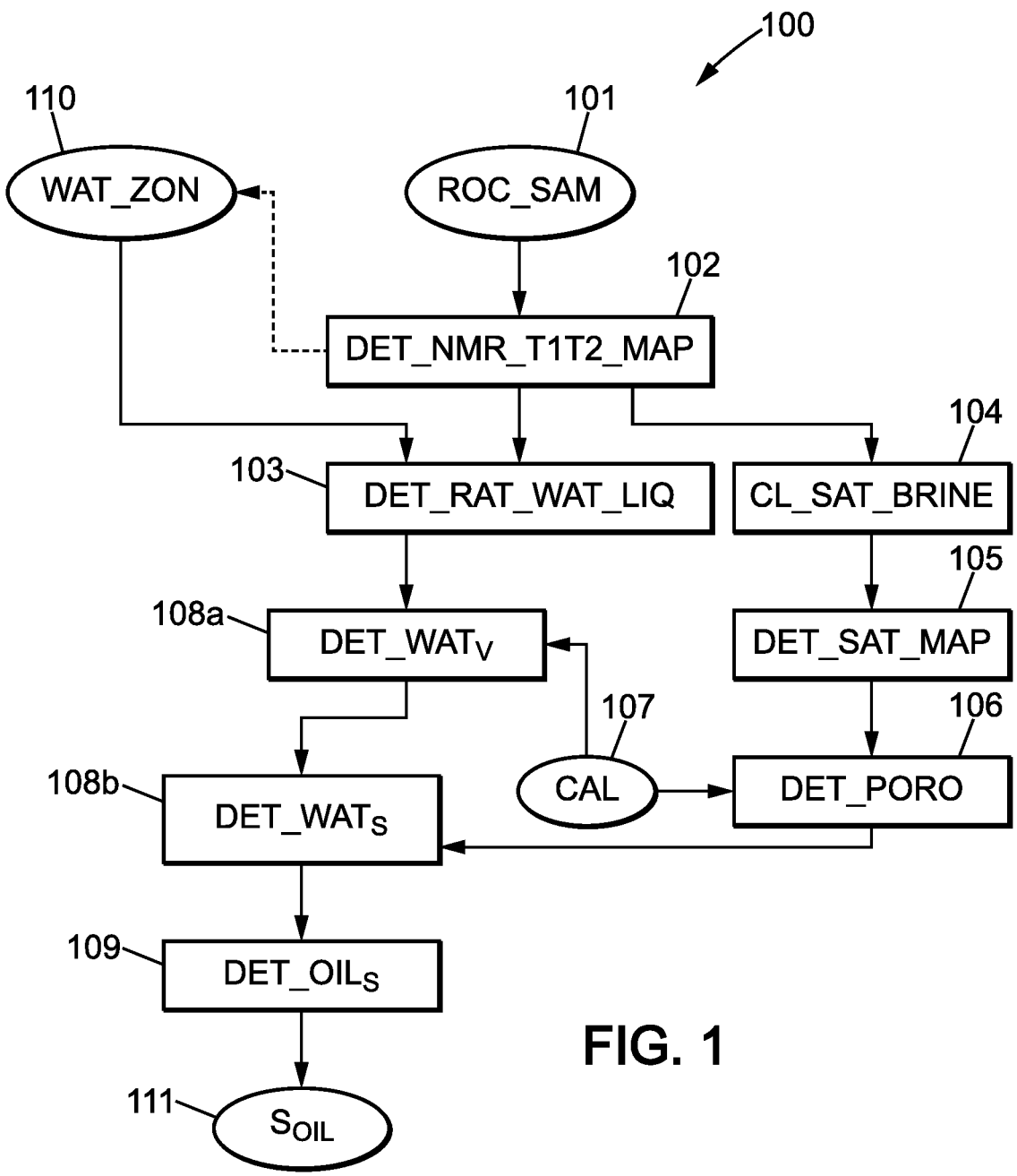
FIG. 1 is a flow chart describing an embodiment of the present invention.

FIG. 1 is a flow chart 100 describing a possible embodiment of the present invention. Part of this flow chart can represent steps of an example of a computer program.

When receiving a rock sample, it is possible to perform a $T_1T_2$ NMR sequence on this sample "as received" (step 102) i.e. with the original liquids captured in the pores of the rock samples.

Figure 2A:
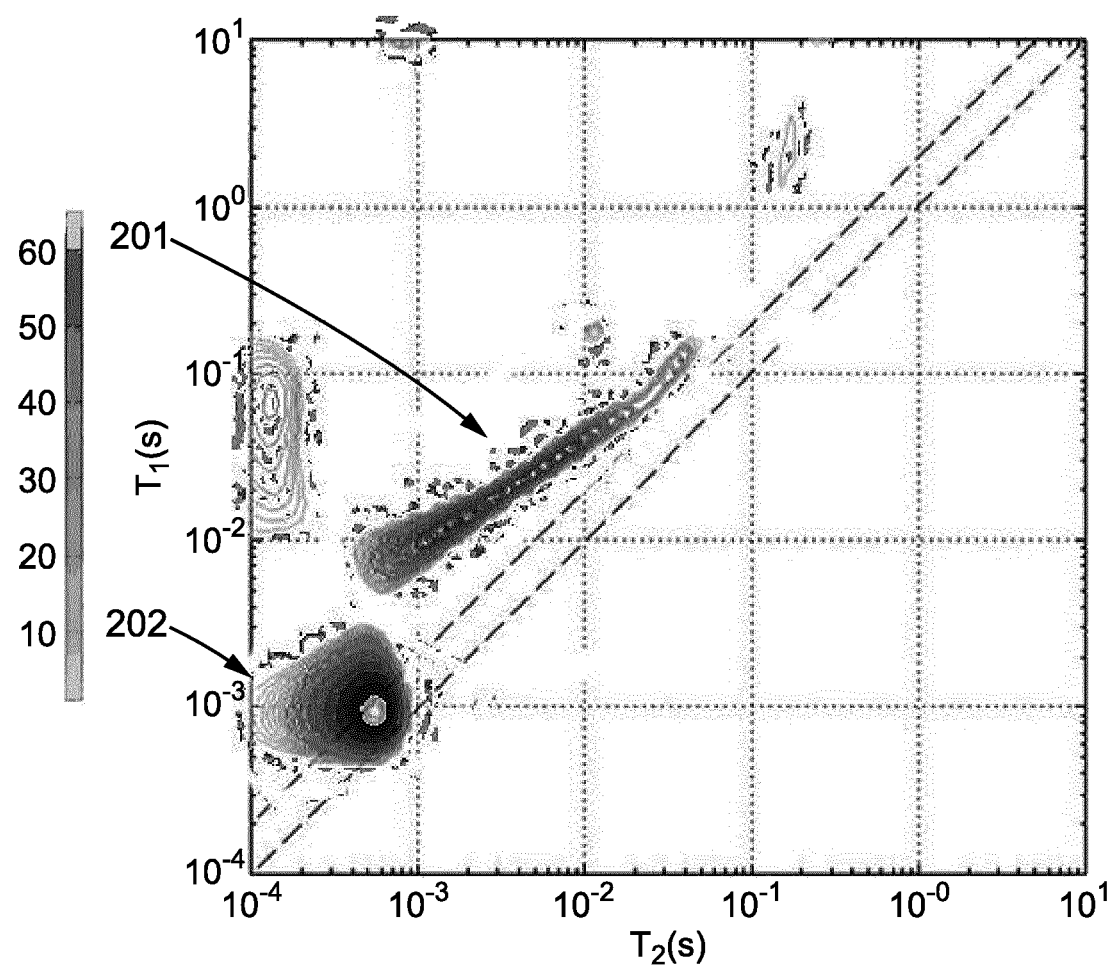
FIG. 2a is a $T_1T_2$ map of a rock sample.

For instance, the obtained $T_1T_2$ map may be represented in FIG. 2a.

It has been noticed that the longitudinal relaxation rates $1/T_1$ and/or the transversal relaxation rates $1/T_2$ for oil and water in confinement allow separating dynamics of these two confined fluids.

It is possible to note that this map comprises two distinct spots (201 and 202), each one of these spots characterizing a different fluid contained in the rock:

the peak (202) at low values of $T_1$, $T_2$ may be assigned to a highly confined water population. The spot 202 corresponds to water protons and is displayed mainly for $$1 < \frac{T_1}{T_2} < 2.$$

the other elongated peak (201) can thus be assigned to a confined oil population which surprisingly exhibits a high $T_1/T_2$ ratio (At 2.5 MHz, this ratio evolves from 10 to 5 values). The hydrocarbon parts of $T_1T_2$ map are often above the two diagonal $$\text{lines} \frac{T_1}{T_2} > 2.$$

Figure 2B:
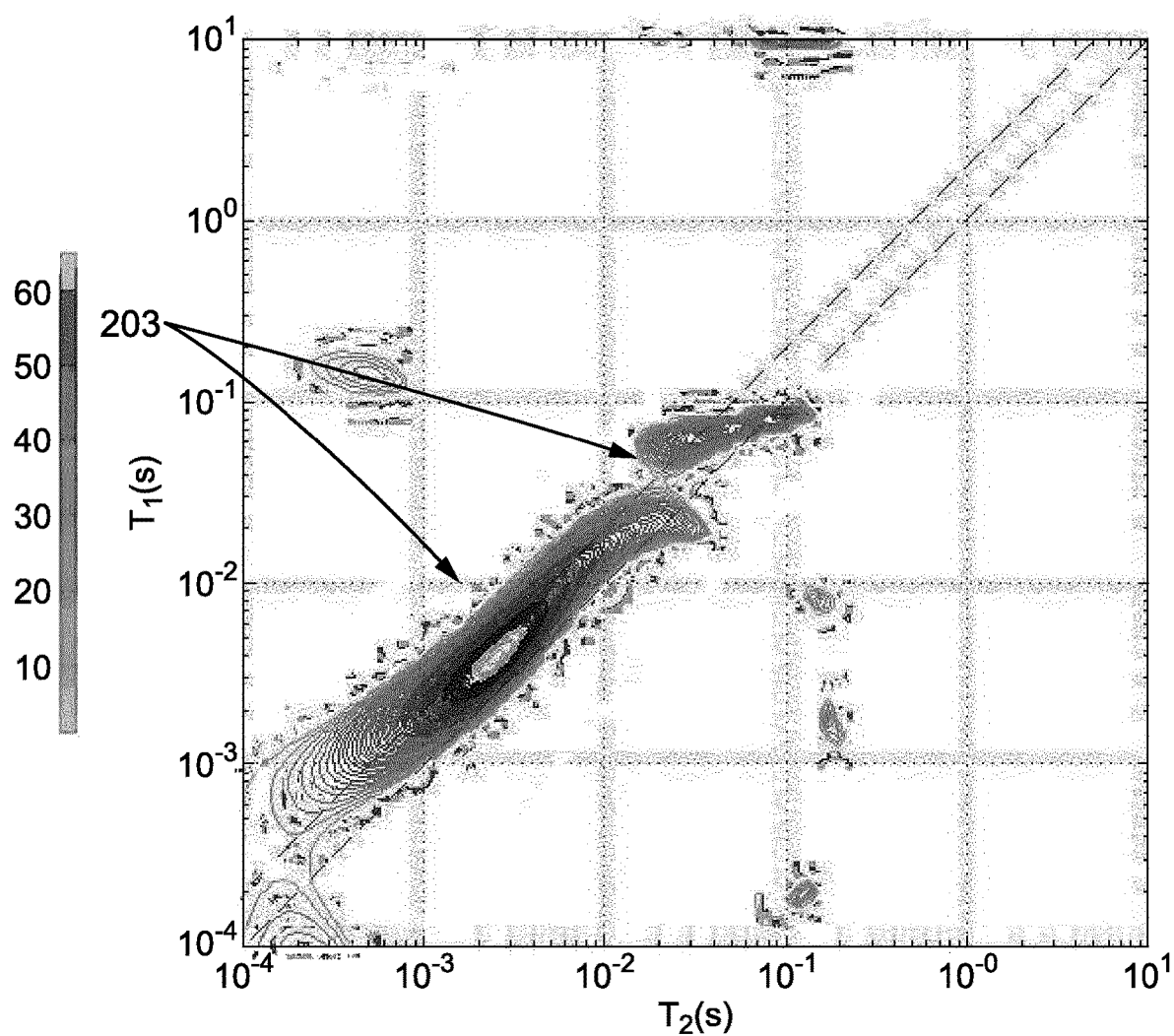
FIG. 2b is a $T_1T_2$ map of a rock sample after a complete saturation with water.
Figure 2C:
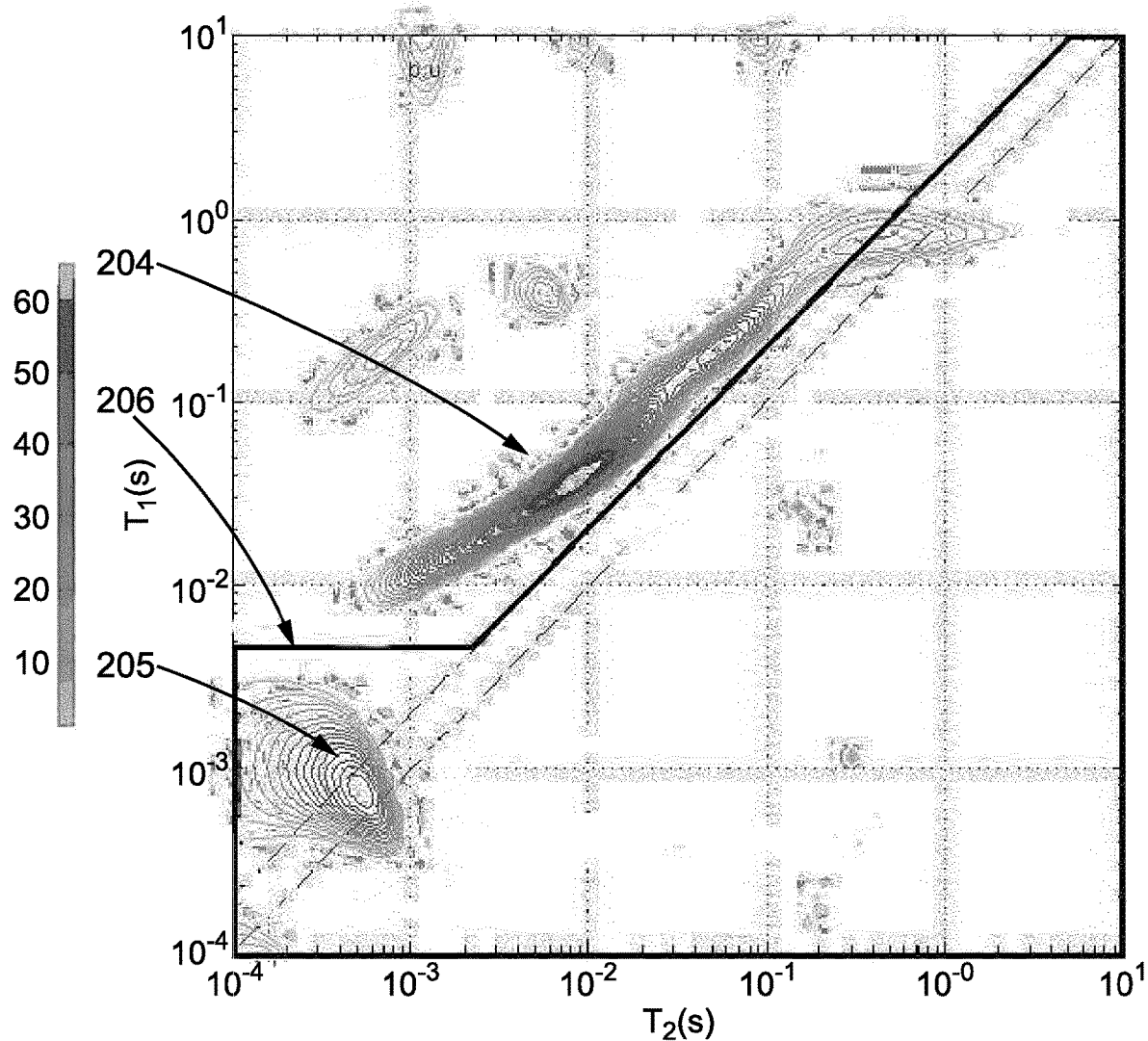
FIG. 2c is a $T_1T_2$ map of a rock sample after washing, low temperature drying and complete saturation with oil.

In order to support this statement, a study has been performed on the same sample:

(i) after a complete saturation (i.e. saturation of 100%) with water (see FIG. 2b, spots 203);

(ii) after washing, low temperature drying and complete saturation (i.e. saturation of 100%) with oil (see FIG. 2c, spot 204). Spot 205 indicates that there is a very weak signal emitted by the water protons (water saturation 20%): said weak signal is due to the fact that the samples have not been dried at high temperature in order to avoid rock deterioration (i.e. below 60° C.) and due to the fact that 60° C. is not sufficient to allow the evaporation of all water in the clay.

In order to ease the determination of the water parts and the hydrocarbon parts of the $T_1T_2$ map, it is possible to (pre-)compute/(pre-)define "separations" that split the parts from each other (i.e. these separations may be polygons such as element 206 in FIG. 2c. These separations may be of any forms (for instance a potato-shaped curve). These separations may define in the $T_1T_2$ maps a water-zone (i.e. a non-oil zone) and oil zone.

These separations (110) may be specific to one country or in one geographical zone or to one specific rock type.

Based on the received/determined separation between the water parts and the hydrocarbon parts in the $T_1T_2$ maps, it is possible to determine (step 103) the ratio of the volume of water $V_{water}$ over the volume of liquids (i.e. hydrocarbon and water) $v_{liquid} = v_{water} + v_{oil}$ in the tested rock sample.

Figure 2D:
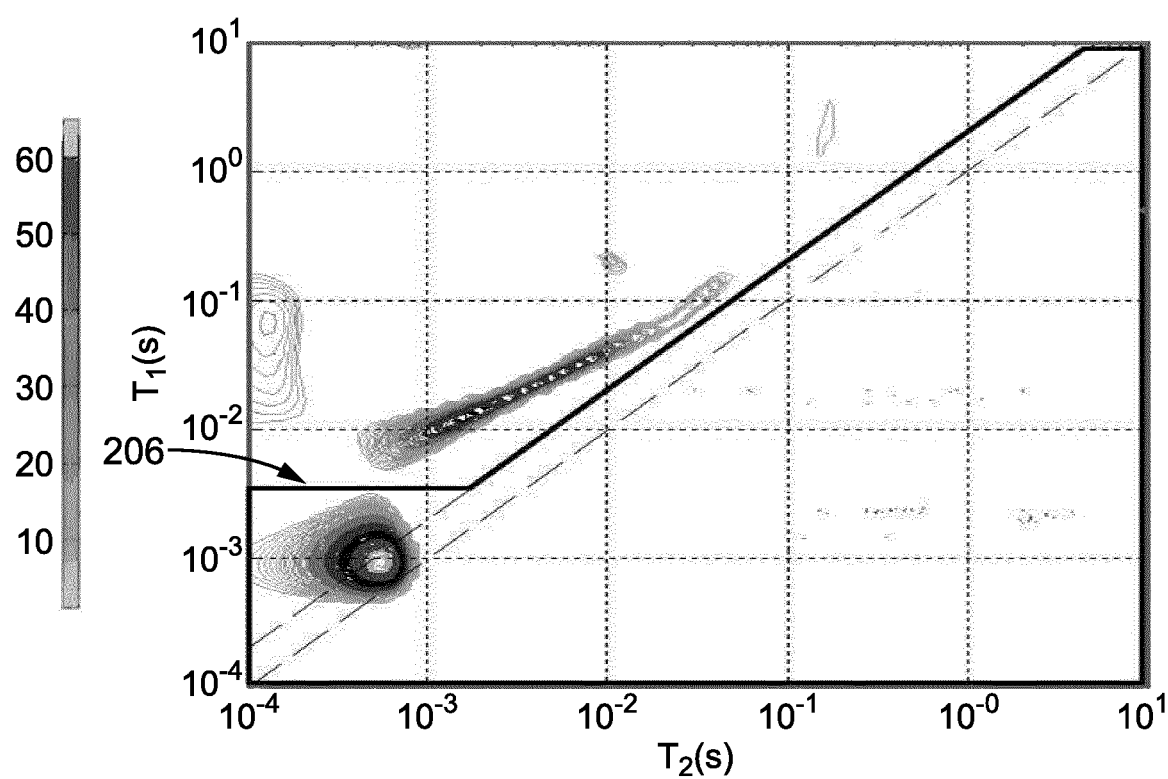
FIG. 2d is a $T_1T_2$ map of a rock sample.

To determine this ratio $$\frac{v_{water}}{v_{water} + v_{oil}},$$

it is possible to determine instead the ratio of the integral of the NMR signal in the polygon 206 over the integral of the NMR signal in the whole $T_1T_2$ map (assuming that the signal is proportional to the liquid volume). For instance, for the given FIG. 2d, the ratio $$\frac{v_{water}}{v_{water} + v_{oil}} = \frac{v_{water}}{v_{liquid}}$$

(and thus the ratio of the integrals) is equal to 0.59.

Step 103 may be optional.

Once this done, it may be advantageous to determine the relation between the quantity of fluid in the rock sample and the related amount of NMR signal emitted.

This relation may be determined by a calibration process: creating a $T_1T_2$ map of 1 cm$^3$ of a given fluid (or a predetermined volume of the given fluid: n cm$^3$). Calibration and saturation of the rock sample is advantageously performed with the same fluid: brine is classically used as saturation fluid.

The calibration factor (107) is noted $$K = \frac{\text{signal}}{cc}$$

(with signal the integral of the amplitude of the NMR signal in the map and cc the volume of liquid analyzed for the calibration (e.g. 1 cm³ or n cm³, see above)).

Knowing the location of water and oil in the $T_1T_2$ map (i.e. the separation 110), and the calibration factor 107 K, it may be possible to compute the water volume $v_{water}$ that is present in the rock sample "as received".

Indeed, the water volume $v_{water}$ is equal to $$\frac{\text{signal}_{water}}{K} = \frac{\text{signal}_{water}}{\text{signal}} cc$$

where $\text{signal}_{water}$ is the integral of the NMR signal in the zone delimited by the separation 110 i.e. where it is assumed that the signal represents the water (step 108a).

In addition, once the calibration factor is determined, it is possible to saturate the rock sample at 100% with said saturation fluid. The saturation fluid (e.g. brine as it is also close to the water inside the rock "as received") is forced to fully saturate the sample (pores) by increasing the pressure up to 100 bar or more.

Figure 2E:
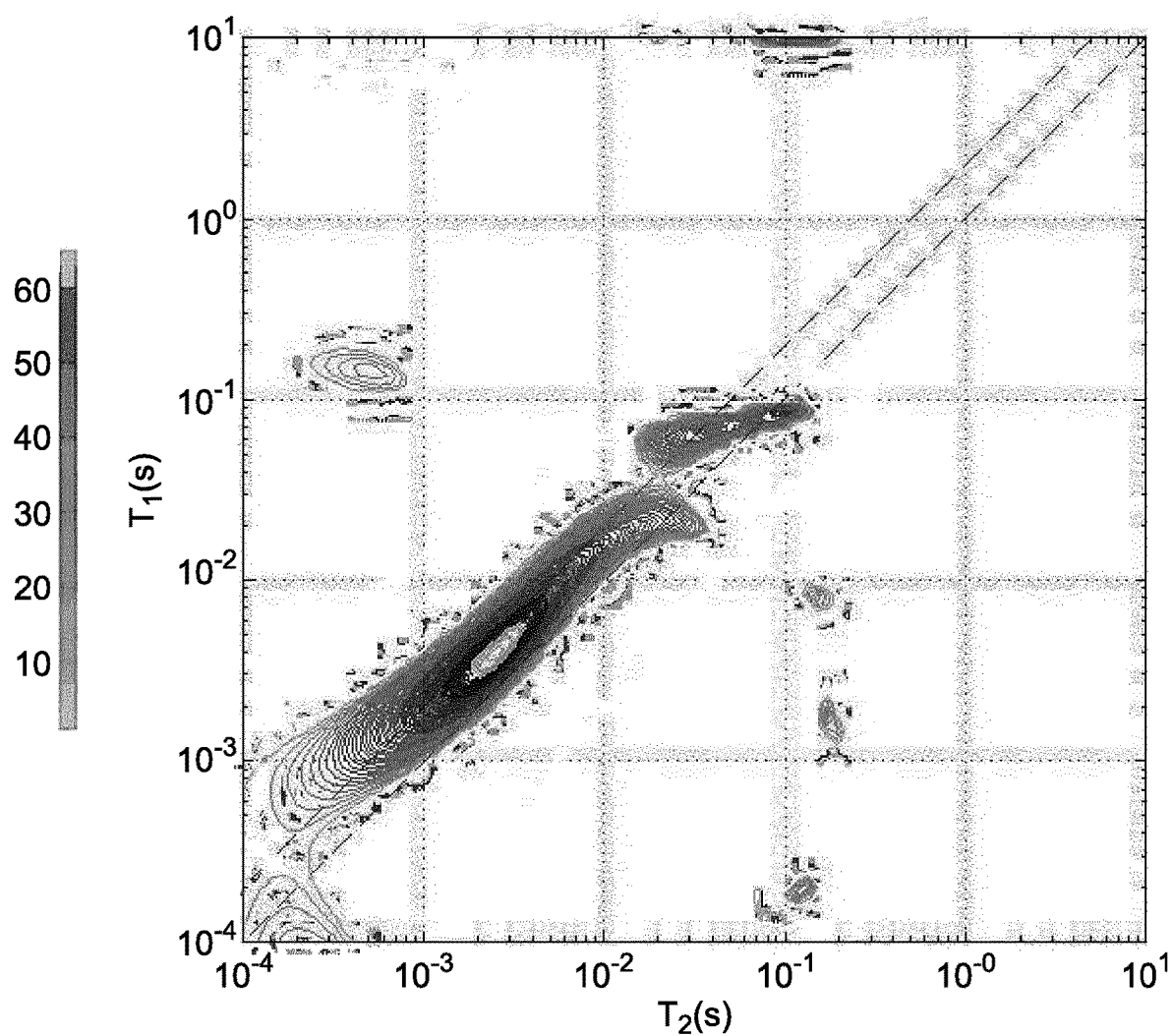
FIG. 2e is a $T_1T_2$ map of a saturated rock sample.

Once the rock sample is saturated, it is possible to compute a $T_1T_2$ map for said saturated sample (step 105, see map shown on FIG. 2e).

By determining the integral of the signal of said latter $T_1T_2$ map (noted $\text{signal}_{brine}$), it is possible to accurately determine the saturation fluid volume in the rock sample i.e.

$$v_{sat} = \frac{\text{signal}_{brine}}{K} = \frac{\text{signal}_{brine}}{\text{signal}} cc.$$

Thus, if the rock sample has a volume of $$v_{sample} \left( = \frac{\pi D^2}{4} L, \right.$$

if the rock sample is a cylinder/plug with D diameter and L length), the porosity of the sample $\phi_{sample}$ may be determined as $$\phi_{sample} = \frac{v_{sat}}{v_{sample}} = \frac{\text{signal}_{brine}}{K \times v_{sample}} = \frac{\text{signal}_{brine}}{\text{signal}} cc \times \frac{1}{v_{sample}}$$

(step 106).

The porosity may be also determined by any known method such as a pycnometry method. It's expressed in p.u (porosity unity) which represents the percentage of the pore volume.

Knowing the porosity $\phi_{sample}$, the volume of water $v_{water}$ in the rock sample and the volume of the rock $v_{sample}$, it may be possible to compute the water saturation $S_{water}$ in the received rock sample 101 (step 108b). Indeed, the water saturation of the sample is $$S_{water} = \frac{v_{water}}{\phi_{sample} \times v_{sample}} = \frac{\text{signal}_{water}}{K \times \phi_{sample} \times \text{sample}}.$$

The oil saturation $S_{oil}$ 111 can thus be determined (step 109) as $S_{oil} = 1 - S_{water}$ and can be returned to the operator for further computations (the determined porosity value $\phi_{sample}$ may also be returned for further processing).

Figure 3:
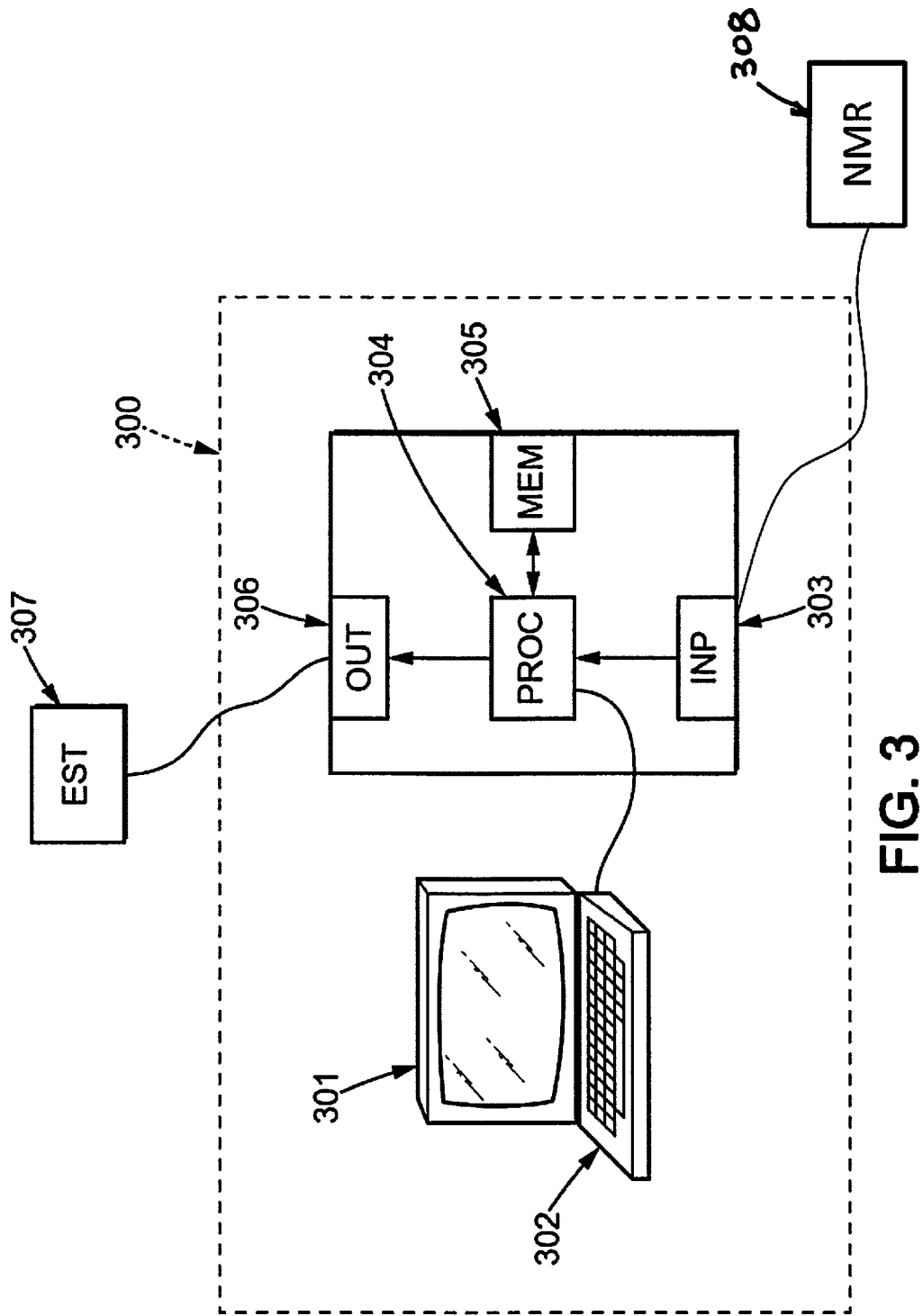
FIG. 3 is an embodiment for a device that enables the present invention.

FIG. 3 is a possible embodiment for a device that enables the present invention.

In this embodiment, the device 300 comprise a computer, this computer comprising a memory 305 to store program instructions loadable into a circuit and adapted to cause circuit 304 to carry out the steps of the present invention when the program instructions are run by the circuit 304.

The memory 305 may also store data and useful information for carrying the steps of the present invention as described above.

The circuit 304 may be for instance:
- a processor or a processing unit adapted to interpret instructions in a computer language, the processor or the processing unit may comprise, may be associated with or be attached to a memory comprising the instructions, or
- the association of a processor/processing unit and a memory, the processor or the processing unit adapted to interpret instructions in a computer language, the memory comprising said instructions, or
- an electronic card wherein the steps of the invention are described within silicon, or
- a programmable electronic chip such as a FPGA chip (for «Field-Programmable Gate Array»).

This computer comprises an input interface 303 for the reception of measurements from the NMR tools 308 and/or the calibration value 107 and/or the separation 110 according to the invention and an output interface 306 for providing for instance the oil saturation value to an estimation tool 307.

To ease the interaction with the computer, a screen 301 and a keyboard 302 may be provided and connected to the computer circuit 304.

Expressions such as "comprise", "include", "incorporate", "contain", "is" and "have" are to be construed in a non-exclusive manner when interpreting the description and its associated claims, namely construed to allow for other items or components which are not explicitly defined also to be present. Reference to the singular is also to be construed in be a reference to the plural and vice versa.

A person skilled in the art will readily appreciate that various parameters disclosed in the description may be modified and that various embodiments disclosed may be combined without departing from the scope of the invention.

The invention claimed is:

1. A method for determining a water saturation value of a rock sample comprising:
   receiving the rock sample;
   receiving a predetermined non-oil zone in a T1T2 map, said non-oil zone being associated to non-oil in said T1T2 map;
   determining a first T1T2 map of said received rock sample using an NMR sequence;
   determining the volume of non-oil in the received rock sample based on an integral in an integration zone of the first T1T2 map, and a calibration value, wherein said integration zone of the first T1T2 map is determined based on the received predetermined non-oil zone;

determining a porosity value of said rock sample; and determining a water saturation value based on the determined volume of non-oil, the determined porosity value and a volume of the rock sample;

wherein the determination of the porosity value is performed by a method comprising:

saturating said rock sample with a saturation fluid;

determining a saturated T1T2 map of the saturated rock sample using an NMR sequence; and determining the porosity value based on an integral in an integration zone of the saturated T1T2 map, the calibration value and the volume of the rock sample;

wherein said integration zone of the saturated T1T2 map is determined based on the received predetermined non-oil zone.

2. The method of claim 1, wherein the porosity value is determined based on a ratio of the integral in the integration zone of the saturated T1T2 map by a product of the calibration value with the volume of the rock sample.

3. The method according to claim 1, wherein the water saturation value is function of a ratio of the determined volume of non-oil by the volume of the rock sample divided by the porosity value.

4. The method according to claim 1, wherein the saturation fluid is brine.

5. The method according to claim 1, wherein the volume of non-oil is determined based on a ratio of the integral in the integration zone of the first T1T2 map by the calibration value.

6. A non-transitory computer readable storage medium, having stored thereon a computer program comprising program instructions, the computer program being loadable into a data-processing unit and adapted to cause the data-processing unit to carry out, when the computer program is run by the data-processing device:

receiving a predetermined non-oil zone in a T1T2 map, said non-oil zone being associated to non-oil in said map;

determining a first T1T2 map of a received rock sample using an NMR sequence; and determining a volume of non-oil in the received rock sample based on an integral in an integration zone of the first T1T2 map, and a calibration value, wherein said integration zone of the first T1T2 map is determined based on the received predetermined non-oil zone;

determining a porosity value of said rock sample; and determining a water saturation value based on the determined volume of non-oil, the determined porosity value and a volume of the rock sample;

wherein the determination of the porosity value is performed by a method comprising:

saturating said rock sample with a saturation fluid;

determining a saturated T1T2 map of the saturated rock sample using an NMR sequence; and determining the porosity value based on an integral in an integration zone of the saturated T1T2 map, the calibration value and the volume of the rock sample;

wherein said integration zone of the saturated T1T2 map is determined based on the received predetermined non-oil zone.

7. A device for determining a non-oil volume of a rock sample comprising:

an interface for receiving a predetermined non-oil zone in a T1T2 map, said predetermined non-oil zone being associated to non-oil in said map;

a NMR device for determining a first T1T2 map of said received rock sample using an NMR sequence;

a circuit for determining a volume of non-oil in the received rock sample based on an integral in an integration zone of the first T1T2 map, said integration zone of the first T1T2 map being determined based on the received predetermined non-oil zone, and a calibration value;

a circuit for determining a porosity value of said rock sample; and a circuit for determining a water saturation value based on the determined volume of non-oil, the determined porosity value and a volume of the rock sample;

wherein the device performs the determination of the porosity value by the use of:

a circuit for determining a saturated T1T2 map of the rock sample that is saturated with a saturation fluid using an NMR sequence; and a circuit for determining the porosity value based on an integral in an integration zone of the saturated T1T2 map, the calibration value and the volume of the rock sample;

wherein said integration zone of the saturated T1T2 map is determined based on the received predetermined non-oil zone.

* * * * *

UNITED STATES PATENT AND TRADEMARK OFFICE
CERTIFICATE OF CORRECTION

PATENT NO. : 10,534,055 B2
APPLICATION NO. : 15/320083
DATED : January 14, 2020
INVENTOR(S) : Nicot et al.

Page 1 of 1

It is certified that error appears in the above-identified patent and that said Letters Patent is hereby corrected as shown below:

On the Title Page

In the Abstract, Line 5:
Delete the ";" following the word map and insert a --.--.

In the Abstract, Line 8:
Delete the word "firstNMR" and insert the words --first NMR--.

Signed and Sealed this
Tenth Day of March, 2020

Andrei Iancu
*Director of the United States Patent and Trademark Office*